United States Patent
Landeka et al.

(10) Patent No.: US 11,427,533 B2
(45) Date of Patent: Aug. 30, 2022

(54) CRYSTALLINE POLYMORPHS OF BARDOXOLONE METHYL

(71) Applicant: PLIVA HRVATSKA d.o.o., Zagreb (HR)

(72) Inventors: Ivana Landeka, Zagreb (HR); Helena Ceric, Zagreb (HR)

(73) Assignee: PLIVA HRVATSKA D.O.O., Zagreb (HR)

( * ) Notice: Subject to any disclaimer, the term of this patent is extended or adjusted under 35 U.S.C. 154(b) by 4 days.

(21) Appl. No.: 16/625,111

(22) PCT Filed: Jul. 12, 2018

(86) PCT No.: PCT/US2018/041752
§ 371 (c)(1),
(2) Date: Dec. 20, 2019

(87) PCT Pub. No.: WO2019/014412
PCT Pub. Date: Jan. 17, 2019

(65) Prior Publication Data
US 2020/0223791 A1 Jul. 16, 2020

Related U.S. Application Data

(60) Provisional application No. 62/581,838, filed on Nov. 6, 2017, provisional application No. 62/551,544, filed on Aug. 29, 2017, provisional application No. 62/532,066, filed on Jul. 13, 2017.

(51) Int. Cl.
*C07C 253/30* (2006.01)
*C07C 255/47* (2006.01)

(52) U.S. Cl.
CPC .......... *C07C 255/47* (2013.01); *C07C 253/30* (2013.01)

(58) Field of Classification Search
CPC .. C07B 2200/13; C07J 63/008; C07C 253/30; C07C 255/47
See application file for complete search history.

(56) References Cited

U.S. PATENT DOCUMENTS

| | | |
|---|---|---|
| 6,326,507 B1 | 12/2001 | Gribble et al. |
| 7,863,327 B2 | 1/2011 | Gribble et al. |
| 8,088,824 B2 | 1/2012 | Walling et al. |
| 8,309,601 B2 | 11/2012 | Walling et al. |
| 8,633,243 B2 | 1/2014 | Walling et al. |
| 8,981,144 B2 | 3/2015 | Gribble et al. |

FOREIGN PATENT DOCUMENTS

| | | |
|---|---|---|
| CN | 102875634 A | 1/2013 |
| CN | 102887936 A | 1/2013 |
| CN | 106560473 A | 4/2017 |
| WO | 2009023232 A1 | 2/2009 |
| WO | 2009023845 A2 | 2/2009 |
| WO | 2010093944 A2 | 8/2010 |

OTHER PUBLICATIONS

Lothar Bore et al., "The anti-inflammatory triterpenoid methyl 2-cyano-3,12-dioxooleana-1,9(11)-dien-28-oate methanol solvate hydrate", Acta Crystallographica Section C, Crystal Structure Communications, Apr. 2002, 12 pages.
Tadashi Honda et al., "Synthetic Oleanane and Ursane Triterpenoids wih Modified Rings A and C: A Series of Highly Active Inhibitors of Nitric Oxide Production in Mouse Macrophages", Journal of Medicinal Chemistry, vol. 43, No. 22, 2000, pp. 4233-4246.
Tadashi Honda et al., "Design and synthesis of 2-cyano-3,12-dioxoolean-1,9-dien-28-oic acid, a novel and highly active inhibitor of nitric oxide production in mouse macrophages", Bioorganic & Medicinal Chemistry Letters, vol. 8, No. 19, Oct. 6, 1998 pp. 2711-2714.
International Search Report for International Application No. PCT/US2018/041752, International Filing Date Jul. 12, 2018, dated Nov. 13, 2018, 8 pages.
Written Opinion for International Application No. PCT/US2018/041752, International Filing Date Jul. 12, 2018, dated Nov. 13, 2018, 9 pages.

*Primary Examiner* — Sun Jae Yoo
(74) *Attorney, Agent, or Firm* — Cantor Colburn LLP

(57) ABSTRACT

Disclosed are crystalline polymorphs of Bardoxolone methyl, and pharmaceutical compositions thereof.

12 Claims, 3 Drawing Sheets

Figure 1. XRPD of Bardoxolone methyl Form C (obtained according to Example 1).
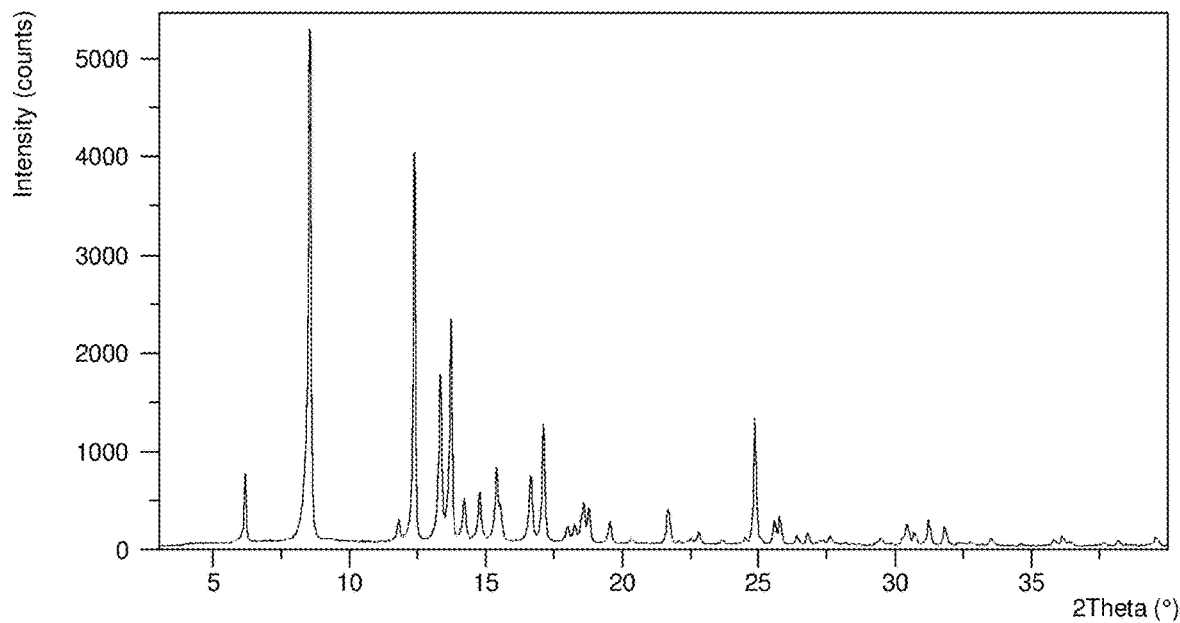
Figure 2. XRPD of Bardoxolone methyl Form D (obtained according to Example 2).
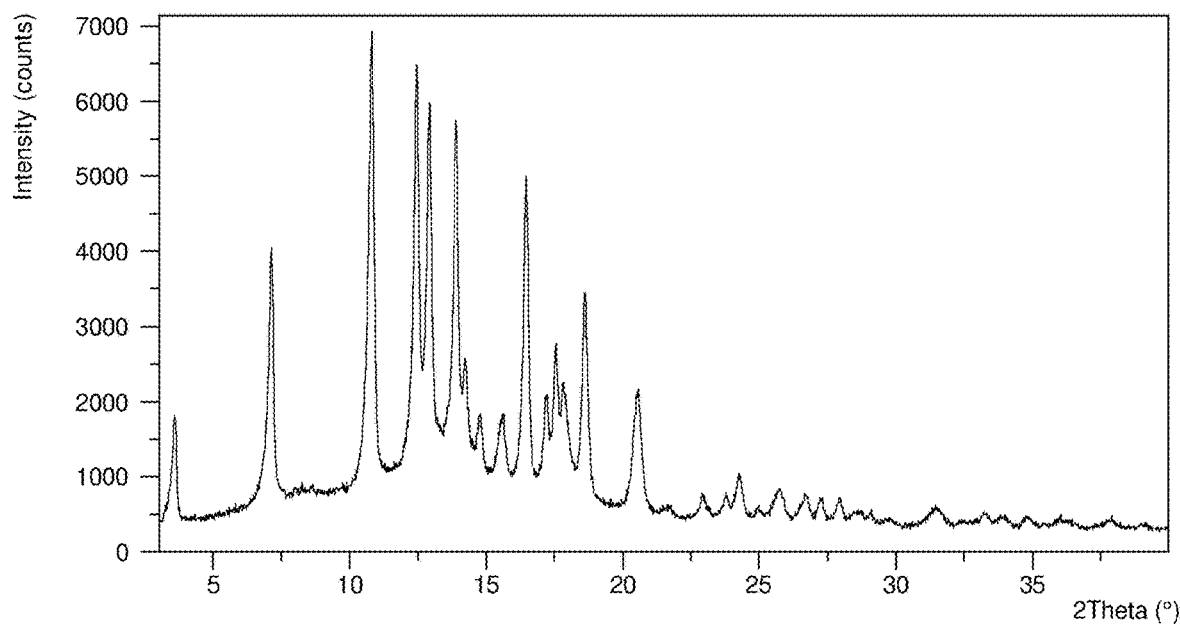

Figure 3. XRPD of Bardoxolone methyl Form E (obtained according to Example 3).
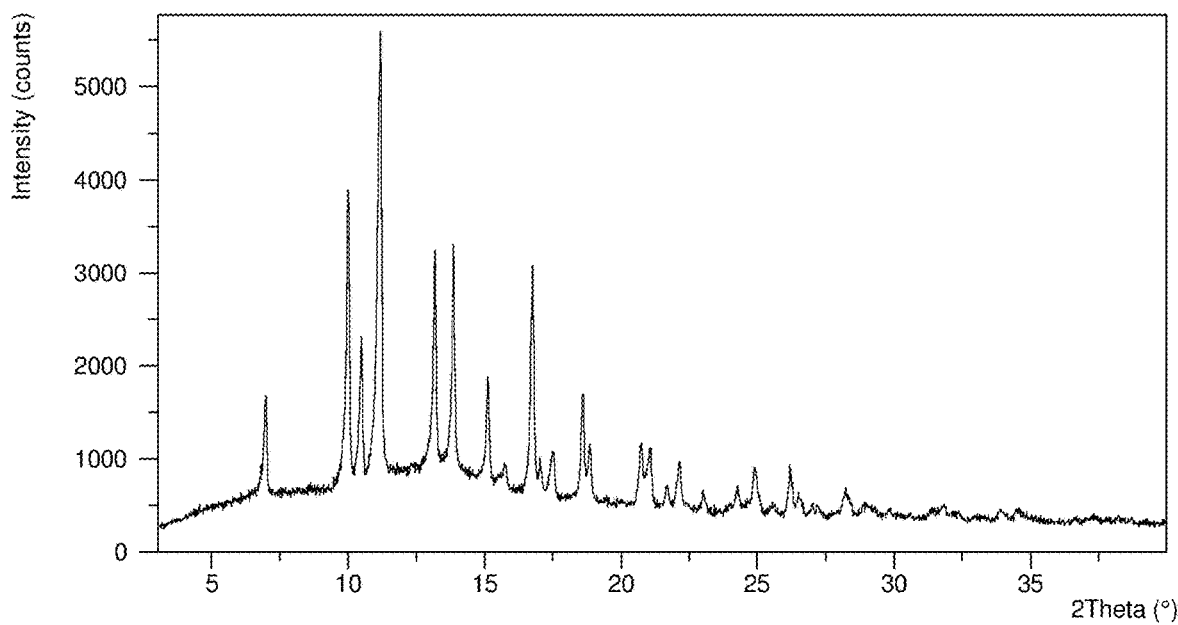
Figure 4. Raman spectrum of Bardoxolone methyl Form D
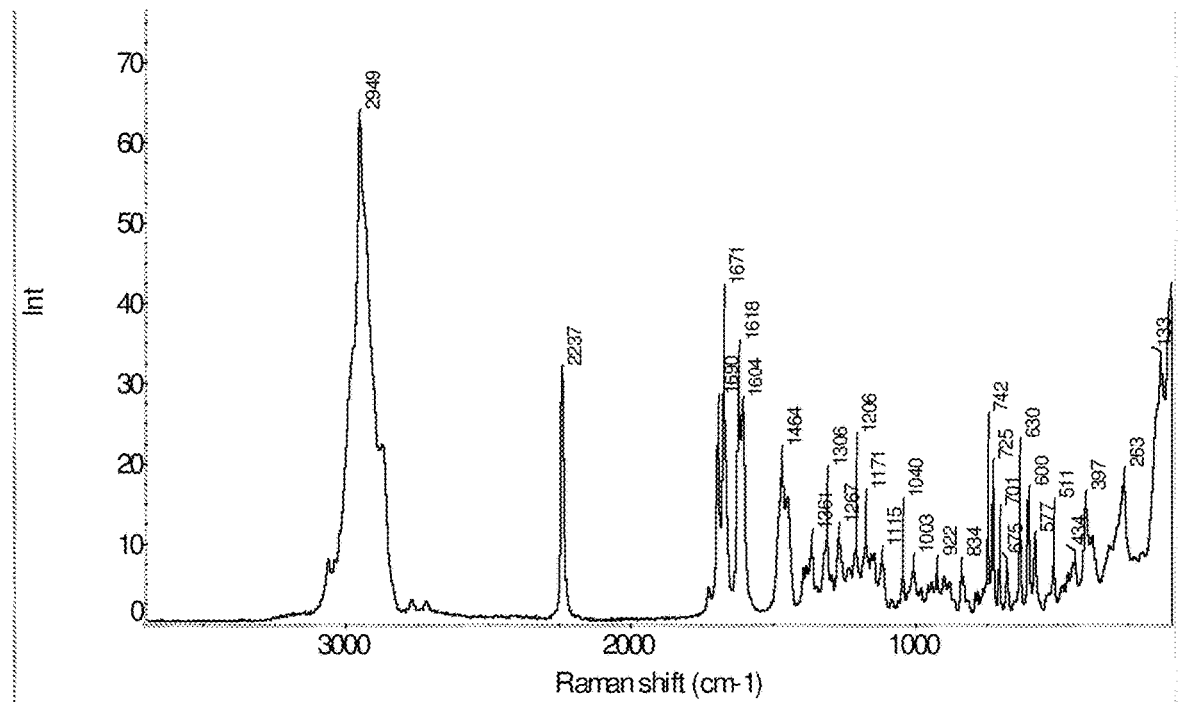

Figure 5. Raman spectrum of Bardoxolone methyl Form D at a range of 3300 to 1400 cm$^{-1}$
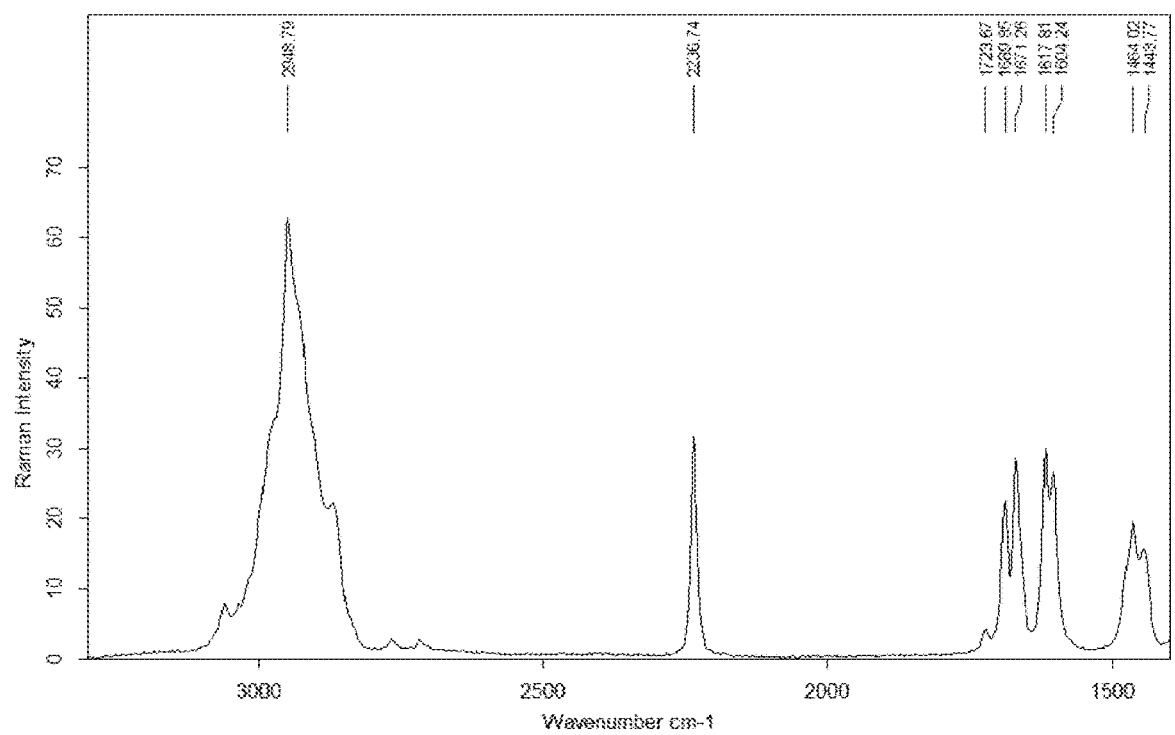

CRYSTALLINE POLYMORPHS OF BARDOXOLONE METHYL

CROSS-REFERENCE TO RELATED APPLICATIONS

This application is a National Stage application of PCT/US2018/041752, filed Jul. 12, 2018, and is related to, and claims the benefit of priority of, U.S. Provisional Patent Application No. 62/581,838, filed Nov. 6, 2017, 62/551,544, filed Aug. 29, 2017, and 62/532,066, filed Jul. 13, 2017, the contents of each are incorporated herein by reference in their entirety for all purposes.

FIELD OF THE DISCLOSURE

The present disclosure encompasses crystalline polymorphs of Bardoxolone methyl, and pharmaceutical compositions thereof.

BACKGROUND OF THE DISCLOSURE

Bardoxolone methyl chemical name is Methyl-2-cyano-3,12-dioxooleana -1,9(11)-dien-28-oic acid, having the following chemical structure:

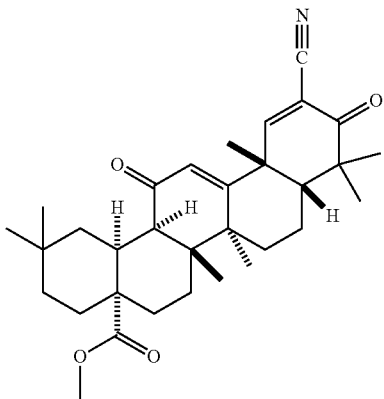

Bardoxolone methyl is an oral synthetic triterpenoid, under development for the treatment of certain pathologies, e.g.: connective tissue disease-associated pulmonary arterial hypertension (CTD-PAH), pulmonary arterial hypertension, hereditary nephritis, diabetic kidney disease, chronic kidney disease, and Alport syndrome.

The compound is described in European Patent No. EP 1089724. A process for its preparation is described in U.S. Pat. No. 6,326,507, as well as in WO 2013-169553 (U.S. Pat. No. 8,981,144). European Patent No. EP 2187741 and EP 2450057 (U.S. Pat. Nos. 8,088,824, 8,309,601 and 8,633,243) described crystalline forms of Bardoxolone methyl. CN 102887936 (A) and CN 102875634 (B) relate to polymorphic forms. CN-106560473 (A) relates to a process. WO2010093944 relates to dosage compositions.

Polymorphism, the occurrence of different crystalline forms, is a property of some molecules and molecular complexes. A single molecule may give rise to a variety of polymorphs having distinct crystal structures and physical properties like melting point, thermal behaviors (e.g., measured by thermogravimetric analysis—"TGA", or differential scanning calorimetry—"DSC"), X-ray diffraction (XRD) pattern, infrared absorption fingerprint, and solid state (13C) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Bardoxolone methyl which are both stable and soluble.

SUMMARY OF THE DISCLOSURE

The present disclosure provides crystalline polymorphs of Bardoxolone methyl, processes for preparation thereof, and pharmaceutical compositions thereof. These crystalline polymorphs can be used to prepare other forms of Bardoxolone methyl.

The present disclosure provides crystalline polymorphs of Bardoxolone methyl and for use in the preparation of pharmaceutical compositions and/or formulations for use in medicine, preferably for the treatment of conditions associated with chronic inflammation such as pulmonary hypertension, diabetic kidney disease, Alport syndrome, chronic kidney disease, connective tissue disease-associated pulmonary arterial hypertension or hereditary nephritis.

The present disclosure also encompasses the use of crystalline polymorph of Bardoxolone methyl of the present disclosure for the preparation of pharmaceutical compositions and/or formulations.

In another aspect, the present disclosure provides pharmaceutical compositions comprising crystalline polymorph of Bardoxolone methyl according to the present disclosure.

In yet another embodiment, the present disclosure encompasses pharmaceutical formulations comprising the described crystalline polymorph of Bardoxolone methyl, or pharmaceutical compositions comprising the described crystalline polymorph of Bardoxolone methyl and at least one pharmaceutically acceptable excipient.

The present disclosure comprises processes for preparing the above mentioned pharmaceutical compositions. The processes comprise combining crystalline polymorph of Bardoxolone methyl with at least one pharmaceutically acceptable excipient.

The crystalline polymorph of Bardoxolone methyl as defined herein and the pharmaceutical compositions or formulations of the crystalline polymorph Bardoxolone methyl may be used as medicaments, particularly for the treatment of conditions associated with chronic inflammation such as pulmonary hypertension, diabetic kidney disease, Alport syndrome, chronic kidney disease, connective tissue disease-associated pulmonary arterial hypertension or hereditary nephritis.

The present disclosure also provides methods of treating Pulmonary arterial hypertension or hereditary nephritis, comprising administering a therapeutically effective amount of crystalline polymorph Bardoxolone methyl of the present disclosure, or at least one of the above pharmaceutical compositions or formulations, to a subject suffering from Pulmonary arterial hypertension or hereditary nephritis, or otherwise in need of the treatment.

The present disclosure also provides the uses of crystalline polymorph of Bardoxolone methyl of the present disclosure, or at least one of the above pharmaceutical compositions or formulations, for the manufacture of medicaments for treating Pulmonary arterial hypertension or hereditary nephritis.

BRIEF DESCRIPTION OF THE DRAWINGS

FIG. 1 shows a characteristic X-ray powder diffraction pattern (XRPD) of Bardoxolone methyl Form C.

FIG. 2 shows a characteristic X-ray powder diffraction pattern (XRPD) of Bardoxolone methyl Form D.

FIG. 3 shows a characteristic X-ray powder diffraction pattern (XRPD) of Bardoxolone methyl Form E.

FIG. 4 shows a Raman spectrum of Bardoxolone methyl Form D.

FIG. 5 shows a Raman spectrum of Bardoxolone methyl Form D at a range of 3300 to 1400 $cm^{-1}$.

DETAILED DESCRIPTION OF THE DISCLOSURE

The present disclosure encompasses crystalline polymorphs of Bardoxolone methyl. Solid state properties of Bardoxolone methyl and crystalline polymorphs thereof can be influenced by controlling the conditions under which Bardoxolone methyl and crystalline polymorphs thereof are obtained in solid form.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, a crystalline polymorph of Bardoxolone methyl described herein as substantially free of any other solid state forms would be understood to contain greater than about 80% (w/w), greater than about 90% (w/w), greater than about 95% (w/w), greater than about 98% (w/w), greater than about 99% (w/w), or about 100% (w/w) of the subject crystalline polymorph of Bardoxolone methyl. In some embodiments of the disclosure, the described crystalline polymorph of Bardoxolone methyl may contain from about 1% to about 20% (w/w), from about 5% to about 20% (w/w), or from about 5% to about 10% (w/w) of one or more other crystalline polymorph of the same Bardoxolone methyl.

Depending on which other crystalline polymorphs a comparison is made, the crystalline polymorphs of Bardoxolone methyl of the present disclosure has advantageous properties selected from at least one of the following: chemical purity, flowability, solubility, dissolution rate, morphology or crystal habit, stability—such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility, and bulk density.

A solid state form, such as a crystal form or an amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Bardoxolone methyl referred to herein as being characterized by graphical data "as depicted in" or "as substantially depicted in" a Figure will thus be understood to include any crystal forms of Bardoxolone methyl characterized with the graphical data having such small variations, as are well known to the skilled person, in comparison with the Figure.

As used herein, and unless stated otherwise, the term "anhydrous" in relation to crystalline forms of Bardoxolone methyl, relates to a crystalline form of Bardoxolone methyl which does not include any crystalline water (or other solvents) in a defined, stoichiometric amount within the crystal. Moreover, an "anhydrous" form would typically not contain more than 1% (w/w), of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, and unless indicated otherwise, the term "wet crystalline form" refers to a polymorph that was not dried using any conventional techniques to remove residual solvent. Examples for such conventional techniques can be, but not limited to, evaporation, vacuum drying, oven drying, drying under nitrogen flow etc.

As used herein, and unless indicated otherwise, the term "dry crystalline form" refers to a polymorph that was dried using any conventional techniques to remove residual solvent. Examples for such conventional techniques can be, but not limited to, evaporation, vacuum drying, oven drying, drying under nitrogen flow etc.

As used herein, the term "isolated" in reference to crystalline polymorph of Bardoxolone methyl of the present disclosure corresponds to a crystalline polymorph of Bardoxolone methyl that is physically separated from the reaction mixture in which it is formed.

As used herein, unless stated otherwise, the XRPD measurements are taken using copper Kα radiation wavelength 1.54184 Å. XRPD peaks reported herein are measured using CuK α radiation, λ=1.5418 Å, at a temperature of 25±3° C.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours.

As used herein, the term "reduced pressure" refers to a pressure that is less than atmospheric pressure. For example, reduced pressure is about 10 mbar to about 50 mbar.

As used herein and unless indicated otherwise, the term "ambient conditions" refer to atmospheric pressure and a temperature of 18-25° C., or preferably 22-24° C.

The present disclosure comprises a crystalline polymorph of Bardoxolone methyl, designated Form C. The crystalline Form C of Bardoxolone methyl may be characterized by data selected from one or more of the following: an X-ray powder diffraction pattern substantially as depicted in FIG. 1; an X-ray powder diffraction pattern having peaks at 6.2, 12.4, 15.4, 18.6 and 24.9 degrees 2-theta±0.2 degrees 2-theta; and combinations of these data.

Crystalline Form C of Bardoxolone methyl may be further characterized by an X-ray powder diffraction pattern having peaks at 6.2, 12.4, 15.4, 18.6 and 24.9 degrees 2-theta±0.2 degrees 2-theta, and also having any one, two, three, four or five additional peaks selected from the group consisting of 8.6, 13.3, 13.7, 17.1 and 21.7 degrees 2-theta±0.2 degrees 2-theta.

Crystalline Form C of Bardoxolone methyl may be characterized by an X-ray powder diffraction pattern having peaks at 6.2, 8.6, 12.4, 13.3, 13.7, 15.4, 17.1, 18.6, 21.7 and 24.9 degrees 2-theta±0.2 degrees 2-theta.

Crystalline Form C of Bardoxolone methyl may be characterized by each of the above characteristics alone/or by all possible combinations, e.g., an XRPD pattern having peaks at 6.2, 12.4, 15.4, 18.6 and 24.9 degrees 2-theta±0.2 degrees 2-theta; an XRPD pattern as depicted in FIG. 1, and combinations thereof.

In one embodiment of the present disclosure, crystalline Form C of Bardoxolone methyl is isolated.

The present disclosure further comprises a crystalline polymorph of Bardoxolone methyl, designated Form D. The crystalline Form D of Bardoxolone methyl may be characterized by data selected from one or more of the following: an X-ray powder diffraction pattern substantially as depicted in FIG. 2; an X-ray powder diffraction pattern having peaks at 3.6, 7.1, 10.8, 12.4 and 16.5 degrees 2-theta±0.2 degrees 2-theta; and combinations of these data.

Crystalline Form D of Bardoxolone methyl may be further characterized by an X-ray powder diffraction pattern having peaks at 3.6, 7.1, 10.8, 12.4 and 16.5 degrees 2-theta±0.2 degrees 2-theta, and also having any one, two, three, four or five additional peaks selected from the group consisting of 12.9, 13.9, 14.8, 18.6 and 20.6 degrees 2-theta±0.2 degrees 2-theta.

Crystalline Form D of Bardoxolone methyl may also be characterized by an X-ray powder diffraction pattern having peaks at 14.2, 15.6, 17.2, 17.6, 22.9, 23.8, 24.2, 25.8, 26.7 and 27.9.

Crystalline form D of Bardoxolone methyl as defined in any of the embodiments described herein may alternatively or additionally be characterized by data selected from: a Raman spectrum having peaks at 2949, 1671, 1618 and 1464±4 cm$^{-1}$; Raman spectrum as depicted in FIG. 4 and/or FIG. 5; and combinations of these data.

Crystalline Form D of Bardoxolone methyl may also be characterized by an X-ray powder diffraction pattern having peaks at 3.6, 7.1, 10.8, 12.4, 12.9, 13.9, 14.8, 16.5, 18.6, and 20.6 degrees 2-theta±0.2 degrees 2-theta.

Crystalline Form D of Bardoxolone methyl may alternatively or additionally be characterized by a PXRD pattern having peaks at: 3.6, 7.1, 10.8, 12.4, 12.9, 13.9, 14.2, 14.8, 15.5, 15.6, 16.5, 17.2, 17.6, 17.8, 18.6, 20.6, 21.7, 22.9, 23.8, 24.2, 24.9, 25.8, 26.7, 27.3, 27.9, 28.7, 29.1, 29.7, 31.5, 33.3, 33.9, 34.8, 36.0, 37.9 and 39.0 degrees 2-theta±0.2 degrees 2-theta.

Crystalline Form D of Bardoxolone methyl as defined in any embodiment described herein may be characterized by each of the above characteristics alone/or by all possible combinations, e.g., an XRPD pattern having peaks at 3.6, 7.1, 10.8, 12.4 and 16.5 degrees 2-theta±0.2 degrees 2-theta; an XRPD pattern as depicted in FIG. 2, and combinations thereof.

In one embodiment of the present disclosure, crystalline Form D of Bardoxolone methyl as defined in any embodiment described herein is isolated. Crystalline Form D of Bardoxolone methyl according to any of the embodiments described herein may be an anhydrous, non-solvated form.

Crystalline Form D of Bardoxolone methyl is stable at various conditions and is resistant to conversion to any other forms, for example under pressure of 1 t (75 KN/m$^2$) or 2 t (150 KN/m$^2$) for 1 minute, after heating for 5 min to 100° C. and after exposure to water sauna condition (wherein "water sauna condition" refers to room temperature and a relative humidity (RH) of about 90%-100% for 24 hours in a closed flask). Crystalline Form D of Bardoxolone is also stable to conversion after exposure to an atmosphere containing organic solvents, for example ethylene glycol, in a closed vessel at room temperature for 24 hours). Such stability may enable the use of form D in variety of preparation methods including preparation of solid dispersion by spray drying, wet granulation etc.

As indicated in WO2010093944 crystalline Form A has relatively low oral bioavailability, while a non-crystalline form of Bardoxolone methyl ("Form B") shows markedly superior oral bioavailability compared to Form A. Crystalline Form D of the present invention surprisingly showed an improved solubility compared to the crystalline form A and comparable solubility to the non-crystalline form B. This may allow the use of Form D in preparation of different kind of pharmaceutical compositions/formulations.

The present disclosure further comprises a crystalline polymorph of Bardoxolone methyl, designated Form E. The crystalline Form E of Bardoxolone methyl may be characterized by data selected from one or more of the following: an X-ray powder diffraction pattern substantially as depicted in FIG. 3; an X-ray powder diffraction pattern having peaks at 7.0, 13.2, 13.9, 15.1 and 16.8 degrees 2-theta±0.2 degrees 2-theta; and combinations of these data.

Crystalline Form E of Bardoxolone methyl may be further characterized by an X-ray powder diffraction pattern having peaks at 7.0, 13.2, 13.9, 15.1 and 16.8 degrees 2-theta±0.2 degrees 2-theta, and also having any one, two, three, four or five additional peaks selected from the group consisting of 10.0, 10.5, 11.2, 18.6 and 22.1 degrees 2-theta±0.2 degrees 2-theta.

Crystalline Form E of Bardoxolone methyl may be characterized by an X-ray powder diffraction pattern having peaks at 7.0, 10.0, 10.5, 11.2, 13.2, 13.9, 15.1, 16.8, 18.6 and 22.1 degrees 2-theta±0.2 degrees 2-theta, and optionally, additionally by the absence of a peak at 12.0 degrees 2-theta±0.2 degrees two-theta. Crystalline Form E of Bardoxolone methyl may be characterized by each of the above characteristics alone/or by all possible combinations, e.g., an XRPD pattern having peaks at 7.0, 13.2, 13.9, 15.1 and 16.8 degrees 2-theta±0.2 degrees 2-theta; an XRPD pattern as depicted in FIG. 3, and combinations thereof.

Crystalline Form E of Bardoxolone methyl may be further characterized by an X-ray powder diffraction pattern having peaks at 7.0, 13.2, 13.9, 15.1 and 16.8 degrees 2-theta±0.2 degrees 2-theta, and also by the absence of a peak at 12.0 degrees 2-theta±0.2 degrees two-theta.

In one embodiment of the present disclosure, crystalline Form E of Bardoxolone methyl is isolated.

The step of isolating Bardoxolone methyl or crystalline polymorph of Bardoxolone methyl may be performed by crystallization.

The present disclosure provides pharmaceutical composition or formulation comprising any of the above crystalline forms of Bardoxolone methyl or combinations thereof, optionally in combination with any other solid state forms of Bardoxolone methyl such as amorphous or crystalline form. The pharmaceutical composition or formulation is preferably for oral treatment, and more preferably wherein the pharmaceutical composition is in a form of capsules.

The above crystalline polymorphs can be used to prepare other crystalline polymorphs of Bardoxolone methyl.

The present disclosure provides crystalline polymorphs of Bardoxolone methyl for use in the preparation of pharmaceutical compositions comprising Bardoxolone methyl and/or crystalline polymorphs thereof.

The present disclosure also encompasses the use of crystalline polymorph of Bardoxolone methyl of the present disclosure for the preparation of pharmaceutical compositions of crystalline polymorph Bardoxolone methyl and/or crystalline polymorphs thereof.

The present disclosure comprises processes for preparing the above mentioned pharmaceutical compositions/formulations. The processes comprise combining the crystalline polymorphs of Bardoxolone methyl of the present disclosure with at least one pharmaceutically acceptable excipient.

The present invention further encompasses a pharmaceutical composition or formulation which is obtainable by a process selected from the group consisting of:

(A) combining one or a combination of the solid state forms of Bardoxolone methyl of the present invention, preferably crystalline Form D or crystalline Form C, and more preferably crystalline Form D, with a solvent and at least one pharmaceutically acceptable excipient, and removing the solvent to form a solid solution, and optionally further combining the solid solution with one or more pharmaceutically acceptable excipients;

(B) combining one or a combination of the solid state forms of Bardoxolone methyl of the present invention, preferably crystalline Form D or crystalline Form C, and more preferably crystalline Form D and at least one pharmaceutically acceptable excipient and optionally a solvent to form a mixture, and thermally extruding the mixture, and optionally combining the extruded mixture with one or more pharmaceutically acceptable excipients; or (C) combining one or a combination of the solid state forms of Bardoxolone methyl of the present invention, preferably crystalline Form D or crystalline Form C, and more preferably crystalline Form D and at least one pharmaceutically acceptable excipient and a solvent to form a mixture, and spray drying the mixture, and optionally combining the spray-dried mixture with one or more pharmaceutically acceptable excipients.

Pharmaceutical formulations of the present invention contain any one or a combination of the solid state forms of Bardoxolone methyl of the present invention. In addition to the active ingredient, the pharmaceutical formulations of the present invention can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Solt, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present invention include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, the active ingredient and any other solid excipients are dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present invention, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present invention include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present invention is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present invention can be a capsule containing the composition, preferably a powdered or granulated solid composition of the invention, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, but they are not subjected to a final tableting step.

A pharmaceutical formulation of Bardoxolone methyl is preferably formulated for administration to a mammal, preferably a human. Bardoxolone methyl can be formulated, for example, as a viscous liquid solution or suspension, preferably a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The crystalline polymorphs of Bardoxolone methyl and the pharmaceutical compositions/formulation of Bardoxolone methyl of the present disclosure can be used as medicaments, particularly in the treatment of: conditions associated with chronic inflammation such as pulmonary arterial hypertension, diabetic kidney disease, Alport syndrome, chronic kidney disease, connective tissue disease-associated pulmonary arterial hypertension or hereditary nephritis.

The present disclosure also provides methods of treating conditions associated with chronic inflammation such as pulmonary arterial hypertension, diabetic kidney disease, Alport syndrome, chronic kidney disease, connective tissue disease-associated pulmonary arterial hypertension or hereditary nephritis comprising administering a therapeutically effective amount of crystalline polymorph of Bardoxolone methyl of the present disclosure, or at least one of the above pharmaceutical compositions/formulations, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

XRPD Method

Sample after being powdered in a mortar and pestle is applied directly on a silicon plate holder. The X-ray powder diffraction pattern was measured with Philips X'Pert PRO X-ray powder diffractometer, equipped with Cu irradiation source=1.54184 Å (Ångström), X'Celerator (2.022° 2θ) detector.

Scanning parameters: angle range: 3-40 deg., step size 0.0167, time per step 37 s, continuous scan.

Thermogravimetric Analysis ("TGA")

TGA analysis was performed on instruments Mettler Toledo TG-DSC 1 with a heating rate of 10° C./min and under nitrogen flow of 30 mL/min. Standard aluminum open pan was used, sample mass was 3-5 mg.

FT-Raman Spectroscopy ("Raman")

Raman analysis was performed on a Nicolet 6700 interferometer, equipped with NXR FT-Raman modul, CaF2 beamsplitter and a liquid nitrogen cooled Ge detector. Spectra were recorded at a resolution of 4 cm-1. Nd-YAG laser (1064 nm, 500 mW) was used to excite the sample.

Ultra-High Performance Liquid Chromatography ("UHPLC")

UHPLC analyses was performed on Agilent 1290 Infinity LC system with a DAD. UV spectra were recorded at 190-400 nm, with the working wavelength of 240 nm. The column used was Waters Acquity UPLC BEH Phenyl (100 mm×2.1 mm i.d., particle size 1.7 µm), at the column temperature of 50° C. Mobile phases employed for gradient elution were water with 0.1% of formic acid as mobile phase A and acetonitrile with 0.1% of formic acid as mobile phase B. Gradient conditions for the analysis were: isocratic flow from 0.0 to 0.5 min with 40% of mobile phase B; linear gradient from 40% of mobile phase B up to 90% of mobile phase B from 0.5 to 4.0 min; isocratic flow at 90% of mobile phase B from 4.0 to 4.5 min; linear gradient down to 40% of mobile phase B from 4.5 to 5.0 min and finally, reconditioning the column for 0.5 min on starting conditions. 1 µL to 10 µL of sample solution was injected at a flow rate of 0.7 mL min$^{-1}$.

Preparation of Starting Materials

Bardoxolone methyl can be prepared for example as described in U.S. Pat. No. 6,326,507. Bardoxolone methyl (form A) can be prepared for example as described in U.S. Pat. No. 8,309,601. Bardoxolone methyl (form B; glassy) can be prepared for example as described in U.S. Pat. No. 8,088,824. Alternatively Bardoxolone methyl form A may be prepared according to reference example A and Bardoxolone methyl form B may be prepared according to reference example B.

REFERENCE EXAMPLE A

Preparation of Bardoxolone Methyl Form A

Bardoxolone methyl (0.2 g) was dissolved in THF (2.4 mL) at r.t. (room temperature). Solution was added drop wise in heptane (40 mL) at r.t. The obtained suspension was stirred for 24 hours and the solid was filtered.

REFERENCE EXAMPLE B

Preparation of Bardoxolone Methyl Form B

Bardoxolone methyl form A (2.0 g) was milled for 3 h at 800 rpm in a stainless steel jar with 4 stainless steel balls.

EXAMPLE 1

Preparation of Bardoxolone Methyl Form C

Bardoxolone methyl (50±5 mg) was dissolved in 1-methylpyrrolidin-2-one (1 mL) at room temperature (r.t.). The solution was left in an open flask at r.t. for 5 weeks to evaporate. Obtained solid was analyzed by XRPD.

EXAMPLE 2

Preparation of Bardoxolone Methyl Form D

Bardoxolone methyl form A (500 mg) was slurried in methanol (1 mL) at r.t. in a closed flask for 48 days. The solid was filtered, dried in a vacuum oven at 50° C. for 30 min and analyzed by XRPD.

EXAMPLE 3

Preparation of Bardoxolone Methyl Form E

Bardoxolone methyl form A (2.3 g) was dissolved in methanol/water (95:5) mixture (126 mL) by heating to reflux. The solution was cooled down to 0° C. and the formed suspension was filtered. The filtrate was left to evaporate in an open flask at r.t. for 5 days. The obtained precipitate was analyzed by XRPD.

EXAMPLE 4

Preparation of Bardoxolone Methyl Form D

Bardoxolone methyl form B (1.0 g) was slurried in methanol (2 mL) at 10° C. for 2 days. Solid was filtered and analyzed by XRPD.

EXAMPLE 5

Preparation of Bardoxolone Methyl Form D

Bardoxolone methyl form B (1.0 g) was slurried in methanol/MTBE (methyl tert-butyl ether) 1:2 (10 mL) at 10° C. for 4 days. Solid (640 mg) was filtered and analyzed by XRPD.

EXAMPLE 6

Preparation of Bardoxolone Methyl Form D

Bardoxolone methyl form B (4.35 g) was slurried in methanol/MTBE 1:3 (43 mL) at 10° C. for 5 days. Solid (3.0 g) was filtered, dried in a vacuum oven at 70° C. for 4 hours (2.7 g) and analyzed by XRPD.

EXAMPLE 7

Preparation of Bardoxolone Methyl Form D

Bardoxolone methyl form A (2.54 g) was dissolved in methanol/water 5% (220 mL) at about 67° C. The solution was cooled to 0-5° C. Crystallization occurred at about 10° C. The obtained suspension was stirred at 0-5° C. for 2 days. Solid (2.2 g) was filtered, dried in a vacuum oven at 70° C. for 4 hours (1.9 g) and analyzed by XRPD.

EXAMPLE 8

Evaluation of Solubility of Form D and Patent Forms in U.S. Pat. Nos. 8,309,601 and 8,088,824

Solubility of Bardoxolone methyl form D and the patent forms in U.S. Pat. Nos. 8,309,601 and 8,088,824 were determined in aqueous buffers and water. Suspension of tested substance (150 mg/8 mL) was stirred on a shaker (200 rpm) in a closed vial at 37° C. Suspension was filtered and concentration of Bardoxolone methyl in filtrate was determined by UHPLC. Undissolved residue was analyzed by XRPD.

| pH | Buffer |
| --- | --- |
| 1.2 | 0.063M HCl + 2.0 g/L NaCl |
| 4.5 | 0.05M acetate buffer (PhEur) |

Results

| Bardoxolone methyl starting form | Buffer | Time at 37° C. | Concentration mg/mL (UHPLC) |
| --- | --- | --- | --- |
| Form A disclosed in U.S. Pat. No. 8,088,824 | pH 1.2 | 2 h | LTQL |
| Form B disclosed in U.S. Pat. No. 8,309,601 | | | 0.00008 |
| form D | | | 0.00004 |
| Form A disclosed in U.S. Pat. No. 8,088,824 | | 4 h | LTQL |
| Form B disclosed in U.S. Pat. No. 8,309,601 | | | |
| form D | | | |
| Form A disclosed in U.S. Pat. No. 8,088,824 | pH 4.5 | 2 h | LTQL |
| Form B disclosed in U.S. Pat. No. 8,309,601 | | | 0.00004 |
| form D | | | 0.00002 |

Conclusion

Surprisingly, the solubility of Bardoxolone methyl form D was found to be comparable with the amorphous form B disclosed in U.S. Pat. No. 8,309,601. The solubility of form D was found to be higher than the solubility of the crystalline form A disclosed in U.S. Pat. No. 8,088,824.

EXAMPLE 9

Evaluation of Stability of Form D

The physical stability of Form D was investigated at different conditions: in heating, under pressure and by sauna. Results are listed in the tables below:

| PRESSURE | | | |
| --- | --- | --- | --- |
| Initial sample/form | Pressure | Time | XRD |
| form D | 1 t | 1 min | Form D |
| | 2 t | 1 min | Form D |

| HEATING (open vessel) | | | |
| --- | --- | --- | --- |
| Initial sample/form | Temperature | Time | XRD |
| form D | 100° C. | 5 min | Form D |

| TRANSFORMATION BY SAUNA (Closed flask, RT) | | | |
| --- | --- | --- | --- |
| Initial sample/form | Days | Solvent | XRD |
| Form D | 1 | water | Form D |
| | 1 | ethylene glycol | Form D |

All samples were analyzed by XRPD, Form D was maintained.

The invention claimed is:

1. A crystalline form D of Bardoxolone methyl, which is characterized by data selected from one or more of the following:
   (i) a PXRD pattern having peaks at 3.6, 7.1, 10.8, 12.4 and 16.5 degrees 2-theta±0.2 degrees 2-theta; or
   (ii) a PXRD pattern as depicted in FIG. 2.

2. The crystalline form D of Bardoxolone methyl according to claim 1, which is characterized by data selected from one or more of the following:
   (i) one, two, three, four or five additional peaks selected from the group consisting of 12.9, 13.9, 14.8, 18.6 and 20.6 degrees 2-theta±0.2 degrees 2-theta;

(ii) a Raman spectrum having peaks at 2949, 1671, 1618 and 1464±4 cm$^{-1}$;
(iii) a Raman spectrum as depicted in FIG. 4; or
(iv) a Raman spectrum as depicted in FIG. 5.

3. The crystalline form of Bardoxolone methyl according to claim 1, wherein the crystalline form is isolated.

4. The crystalline form D of Bardoxolone methyl according to claim 1, which is non-solvated form.

5. The crystalline form D of Bardoxolone methyl according to claim 1, which is an anhydrous form.

6. The crystalline form of Bardoxolone methyl according to claim 1, which is polymorphically pure.

7. A pharmaceutical composition or formulation comprising crystalline form D of Bardoxolone methyl, which is characterized by data selected from one or more of the following:
a PXRD pattern having peaks at 3.6, 7.1, 10.8, 12.4 and 16.5 degrees 2-theta ±0.2 degrees 2-theta; or
(ii) a PXRD pattern as depicted in FIG. 2.

8. A pharmaceutical composition or formulation according to claim 7 comprising at least one pharmaceutically acceptable excipient.

9. A process for preparing a pharmaceutical composition or formulation according to claim 7 comprising combining the crystalline form D of Bardoxolone methyl and at least one pharmaceutically acceptable excipient.

10. A process for preparing other solid state forms of Bardoxolone methyl comprising preparing the crystalline form D of Bardoxolone methyl according to claim 1 and converting it to an amorphous form of Bardoxolone methyl by spray drying.

11. A method of treating a condition associated with chronic inflammation, comprising administering a therapeutically effective amount of the crystalline form D of Bardoxolone methyl according to claim 1, optionally formulated as a pharmaceutical composition or formulation, to a subject in need thereof.

12. A method of treating pulmonary arterial hypertension, diabetic kidney disease, Alport syndrome, chronic kidney disease, connective tissue disease-associated pulmonary arterial hypertension, or hereditary nephritis, comprising administering a therapeutically effective amount of the crystalline form D of Bardoxolone methyl according to claim 1, optionally formulated as a pharmaceutical composition or formulation, to a subject in need thereof.

* * * * *